US012286615B2

(12) United States Patent
Ding et al.

(10) Patent No.: US 12,286,615 B2
(45) Date of Patent: *Apr. 29, 2025

(54) CELL TRANSFECTION BY PRECISE MECHANICAL MEMBRANE DISRUPTION

(71) Applicant: THE REGENTS OF THE UNIVERSITY OF COLORADO, A BODY CORPORATE, Denver, CO (US)

(72) Inventors: Xiaoyun Ding, Superior, CO (US); Apresio Kefin Fajrial, Boulder, CO (US)

(73) Assignee: THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 18/208,548

(22) Filed: Jun. 12, 2023

(65) Prior Publication Data
US 2023/0340393 A1 Oct. 26, 2023

Related U.S. Application Data

(63) Continuation of application No. 16/875,283, filed on May 15, 2020, now Pat. No. 11,685,891.
(Continued)

(51) Int. Cl.
C12M 1/34 (2006.01)
C12M 1/26 (2006.01)
C12M 3/06 (2006.01)
C12N 15/89 (2006.01)
C12M 1/42 (2006.01)
C12N 5/16 (2006.01)

(52) U.S. Cl.
CPC ............ C12M 41/46 (2013.01); C12M 23/16 (2013.01); C12M 33/04 (2013.01); C12N 15/89 (2013.01); C12M 35/04 (2013.01); C12N 5/16 (2013.01)

(58) Field of Classification Search
CPC ...... C12M 41/46; C12M 23/16; C12M 33/04; C12M 35/04; C12N 5/16
See application file for complete search history.

(56) References Cited

U.S. PATENT DOCUMENTS 11,685,891 B2 * 6/2023 Ding .................. C12N 15/89
435/287.1
2015/0197720 A1 * 7/2015 Chiou .................. C12M 41/08
435/173.6

FOREIGN PATENT DOCUMENTS

WO WO/2016/070136 5/2016
WO WO/2016/077761 5/2016
(Continued)

OTHER PUBLICATIONS

Huang, D. et al. (2019) "Continuous Vector-free Gene Transfer with a Novel Microfluidic Chip and Nanoneedle Array," *Current Drug Delivery* 16(2), 164-170.
(Continued)

Primary Examiner — Michael L Hobbs
(74) Attorney, Agent, or Firm — Medlen & Carroll, LLP

(57) ABSTRACT

The invention relates to a microfluidic poration device having narrow channels slightly smaller than the width of a target cell, wherein the channels are lined with a plurality of nanospikes in a row extending down the middle of the channel, i.e. in a row parallel to the sides of the channel. In one embodiment, one channel may have 2 nanospikes (or 2 nanolancets). Thus, in particular embodiments, the invention provides microfluidic poration devices capable of simultaneously squeezing cells while piercing holes in their membranes for allowing foreign molecules into cells. The holes in porated cells spontaneously close after exiting the channels, thus entrapping the foreign molecules inside of the target cells. This porated cell population has approximately
(Continued)

a 95% viability with greater than 50% containing at least one foreign molecule.

22 Claims, 9 Drawing Sheets

Related U.S. Application Data

(60) Provisional application No. 62/849,420, filed on May 17, 2019.

(56) References Cited

FOREIGN PATENT DOCUMENTS

| WO | WO/2017/173373 | 10/2017 | | |
|----|----|----|----|----|
| WO | WO-2017173373 A1 | * | 10/2017 | ........ B01L 3/502746 |

OTHER PUBLICATIONS

Sharei, A. et al. (2013) "A vector-free microfluidic platform for intracellular delivery," *Proceedings of the National Academy of Sciences* 110(6), 2082.

Sharei, A. et al. (2013) "Supporting Information: A vector-free microfluidic platform for intracellular delivery," *Proceedings of the National Academy of Sciences* 110(6), 1-10.

SQZ Biotechnologies. (2019) "Our Science". CellSqueeze, sqzbiotech.com, https://sqzbiotech.com/our-science/.

Stewart, M. P. et al. (2016) "In vitro and ex vivo strategies for intracellular delivery," *Nature* 538(7624), 183-192.

Williams, R. (2013) "Narrow Straits: Transfecting molecules into cells is as easy as one, two, squeeze," *TheScientist*.

* cited by examiner

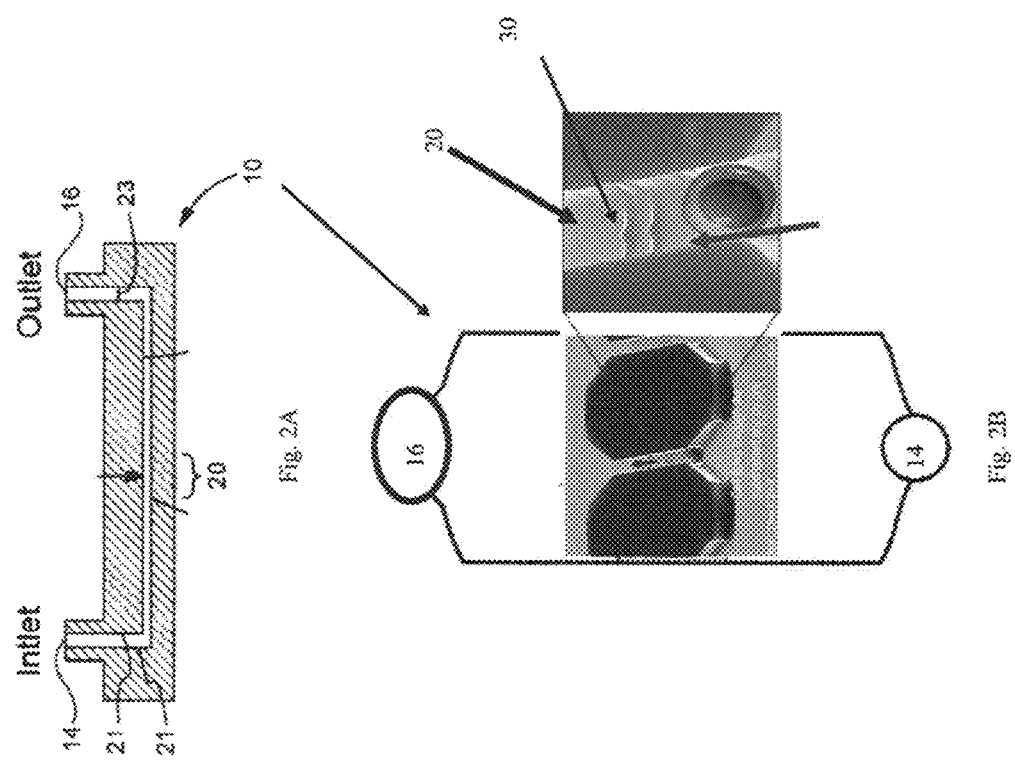

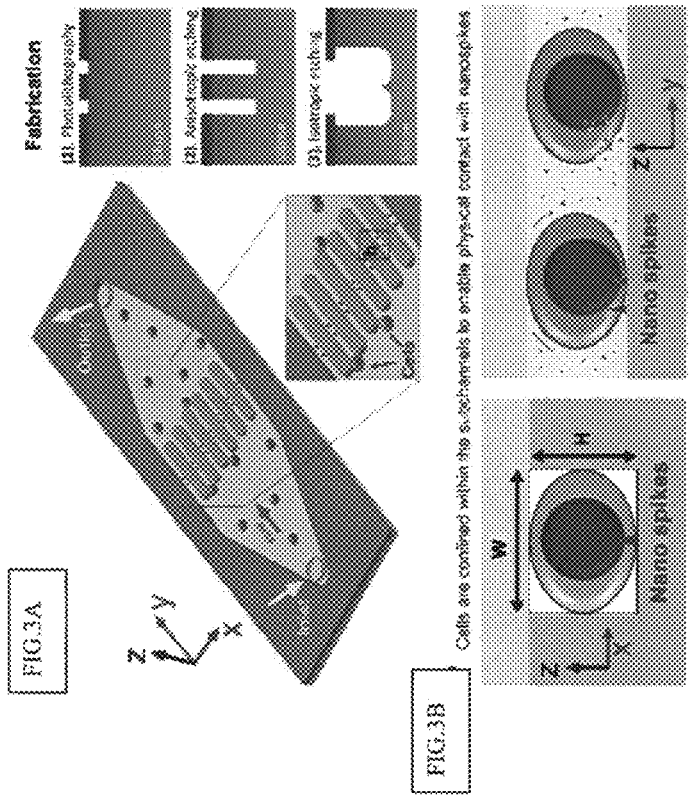
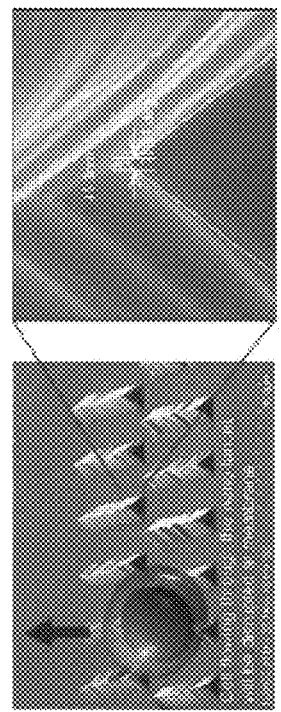
FIG. 3A
FIG. 3B
Fig. 3C

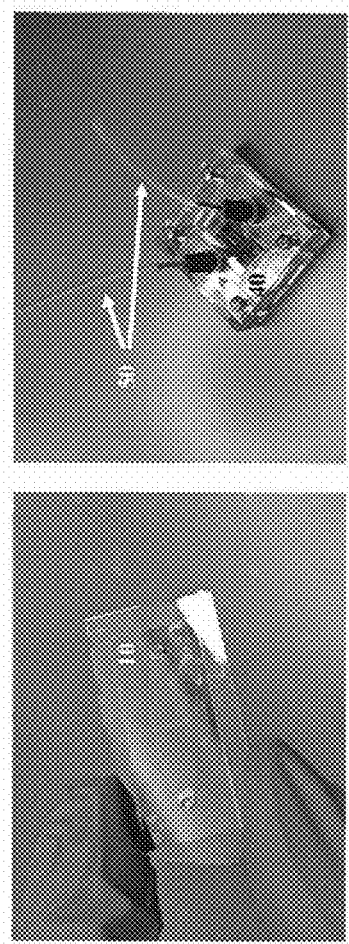

CELL TRANSFECTION BY PRECISE MECHANICAL MEMBRANE DISRUPTION

CROSS-REFERENCE TO RELATED APPLICATIONS

This application is a Continuation of, and claims priority to U.S. patent application Ser. No. 16/875,283 filed May 15, 2020, now U.S. Pat. No. 11,685,891 issued Jun. 27, 2023; which claims benefit of Provisional Application Ser. No. 62/849,420 filed May 17, 2019, the contents of which are incorporated herein in their entirety.

STATEMENT OF RELATED MATTERS

This is a non-provisional parent application filed May 15, 2020 having priority to U.S. Provisional Application Ser. No. 62/849,420 filed May 17, 2019.

FIELD OF THE INVENTION

The invention relates to a microfluidic poration device having a plurality of narrow channels, slightly smaller than the width of a target cell, wherein the channels are lined with a plurality of nanospikes in a row extending down the middle of the channel, i.e. in a row parallel to the sides of the channel. In one embodiment, one channel may have 2 nanospikes (or 2 nanolancets). Thus, in particular embodiments, the invention provides microfluidic poration devices capable of simultaneously squeezing cells while poking holes in their membranes for allowing foreign molecules into cells. The holes in porated cells spontaneously close after exiting the channels, thus entrapping the foreign molecules inside of the target cells. This porated cell population is contemplated to have approximately a 95% viability with greater than 50% containing at least one foreign molecule.

BACKGROUND

Efficient intracellular delivery of exogenous molecules and compounds is one step in the field of cell-based therapies that ideally have efficient and safe techniques to engineer cell functions (FIG. 1). Current delivery systems, largely centered around nucleic acid delivery to cells, have already yielded dramatic progress with plasmid (p) DNA and mRNA for gene expression and small interfering (si) RNA and miRNA for gene silencing in cells. Meanwhile, systematic delivery of protein into living cells, such as active inhibitory antibodies and stimulatory transcription factors, represents a powerful yet largely untapped tool for decoding mechanisms and engineering cell function.

Although nucleic acid and proteins (including a gene-editing complex) are the most widely used materials for engineering cell functions, their efficient delivery to the inside of immune cells is still challenging. For these and other reasons, current methods are limited, with respect to nonlimiting examples of accuracy, efficiency, cost-effectiveness, speed and temporal resolution.

Accordingly, there is a need for new devices and methods that provide a more efficient intracellular delivery with precise dosage control, in particular for delivering large molecules to human immune cells.

SUMMARY OF THE INVENTION

The invention relates to a microfluidic poration device having narrow channels slightly smaller than the width of a target cell, wherein the channels are lined with a plurality of nanospikes in a row extending down the middle of the channel. i.e. in a row parallel to the sides of the channel. In one embodiment, one channel may have 2 nanospikes (or 2 nanolancets). Thus, in particular embodiments, the invention provides microfluidic poration devices capable of simultaneously squeezing cells while poking holes in their membranes for allowing foreign molecules into cells. The holes in porated cells spontaneously close after exiting the channels, thus entrapping the foreign molecules inside of the target cells. This porated cell population has approximately a 95% viability with greater than 50% containing at least one foreign molecule.

In one embodiment, the present invention provides a method of producing modified cells, comprising, a) providing, i) a fluid comprising a compound and a plurality of target cells having a plasma membrane and a cell diameter, ii) a fluidic poration device comprising a plurality of channels each having a central area and a diameter that is less than said cell diameter; iii) a plurality of at least one nanospike/nanolancet, ranging in size from 50 nm to 0.5 micron, positioned on the midline of said central area; b) introducing said fluid into said fluidic poration device such that said target cells move in single file through said channel and said cell diameter is squeezed to match said channel diameter; c) piercing said plasma membrane with said at least one nanospike/nanolancet; d) delivering said compound in a controlled manner to each of said target cells wherein said plasma membrane of each of said target cells is pierced in the same position, the same number of times and to the same depth; d) delivering said compound in a controlled manner to each of said target cells wherein a population of modified target cells is created wherein each of said modified target cells comprise an equivalent amount of said compound. In one embodiment, said plurality of said at least one nanospike/nanolancets are positioned in-series, as a single file row, down the length of the said channel. In one embodiment, said channel is configured as a rectangle. In one embodiment, said nanospike/nanolancet is solid. In one embodiment, said nanospike/nanolancet is not hollow. In one embodiment, said compound is selected from the group consisting of a CRISPR construct, DNA, RNA, siRNA, and a protein. In one embodiment, said two nanospike/nanolancets simultaneously pierce said target cell. In one embodiment, said population of modified target cells is 50%-100% of said plurality of target cells. In one embodiment, said population of modified target cells is 95%-100% viable.

In one embodiment, the present invention provides a method of producing modified cells, comprising: a) providing, i) a fluid comprising a compound and a plurality of target cells having a plasma membrane and a cell diameter, ii) a fluidic poration device comprising a plurality of channels each having a central area and a diameter that is less than said cell diameter; iii) at least one nanospike/nanolancet. ranging in size from 50 nm to 0.5 micron, positioned on the midline of said central area; b) introducing said fluid into said fluidic poration device such that said target cells move in single file through said channel and said cell diameter is squeezed to match said channel diameter; c) piercing said plasma membrane with said at least one nanospike/nanolancet wherein said plasma membrane of each of said target cells is pierced in the same position, the same number of times and to the same depth; d) delivering said compound in a controlled manner to each of said target cells wherein a population of modified target cells is created wherein each of said modified target cells comprise an equivalent amount of said compound.

In one embodiment, the present invention provides a method of producing modified cells, comprising: a) providing, i) a fluid comprising a compound and a plurality of target cells having a plasma membrane and a cell diameter, ii) a fluidic poration device comprising a plurality of channels each having a central area and a diameter that is less than said cell diameter; iii) at least one nanospike/nanolancet, ranging in size from 50 nm to 0.5 micron, positioned on the midline of said central area; b) introducing said fluid into said fluidic poration device such that said target cells move in single file through said channel and said cell diameter is squeezed to match said channel diameter; c) piercing said plasma membrane with said at least one nanospike/nanolancet wherein said plasma membrane of each of said target cells is pierced in the same position, the same number of times and to the same depth; d) delivering said compound in a controlled manner to each of said target cells wherein a population of modified target cells is created wherein each of said modified target cells comprise an equivalent amount of said compound.

Definitions

To facilitate the understanding of this invention, a number of terms are defined below. Terms defined herein have meanings as commonly understood by a person of ordinary skill in the areas relevant to the present invention. Terms such as "a", "*an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "channels" or "microchannels" or "subchannels" as used herein, refer to pathways (whether straight, curved, single, multiple, in a network, etc.) through a medium (e.g., silicon, glass, polymer, etc.) that allow for movement of liquids and gasses. In some embodiments, described herein, "first channel" and "second channel" are used and these need not have the same shape throughout their length. For example, one can change the channel cross-section, curve or split the channel. Channels can connect or be coupled with other components, i.e., keep components "in communication" and more particularly, "in fluidic communication" and still more particularly, "in liquid communication." Such components include, but are not limited to, liquid-intake ports and liquid outlet ports. "Microchannels" are channels with dimensions less than 1 millimeter and greater than 1 micron. It is not intended that the present invention be limited to certain microchannel geometries.

The term "microfluidic" as used herein, relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels.

In a related aspect. "microfluidic device" is used to describe a substrate comprising at least one channel and may comprise other defined components including surfaces and points of contact between solutions including, but not limited to, reagents, buffers and/or test compounds.

The term "fluid" as used herein, refers to an aqueous solution consisting of a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of chemical applications.

The term "fluid mixture" or "fluid system" as used herein, refers to an aqueous solution consisting of a mixture of at least two weak acids and their conjugate base, or vice versa. The mixture pH changes very little over a wide temperature range (e.g., for example, 1-70° C.) due to buffer-buffer interactions that maintain an overall balanced buffer mixture/system pKa. A buffer mixture/system may also contain other components including, but not limited to, salts, ions, metals and/or supplemental buffer molecules.

The term "attached" as used herein, refers to any interaction between a medium (or carrier) and a drug. Attachment may be reversible or irreversible. Such attachment includes, but is not limited to, covalent bonding, ionic bonding. Van der Waals forces or friction, and the like.

The term "drug", "agent" or "compound" as used herein, refers to any pharmacologically active substance capable of being administered that achieves a desired effect. Drugs or compounds can be synthetic or naturally occurring, non-peptide, proteins or peptides, oligonucleotides or nucleotides, polysaccharides or sugars. The term "protein" as used herein, refers to any of numerous naturally occurring extremely complex substances (as an enzyme or antibody) that consist of amino acid residues joined by peptide bonds, contain the elements carbon, hydrogen, nitrogen, oxygen, usually sulfur. In general, a protein comprises amino acids having an order of magnitude within the hundreds.

The term "peptide" as used herein, refers to any of various amides that are derived from two or more amino acids by combination of the amino group of one acid with the carboxyl group of another and are usually obtained by partial hydrolysis of proteins. In general, a peptide comprises amino acids having an order of magnitude with the tens.

The term "polypeptide" refers to any of various amides that are derived from two or more amino acids by combination of the amino group of one acid with the carboxyl group of another and are usually obtained by partial hydrolysis of proteins. In general, a peptide comprises amino acids having an order of magnitude with the tens or larger.

The term, "purified" or "isolated as used herein, may refer to a peptide composition that has been subjected to treatment (i.e., for example, fractionation) to remove various other components, and which composition substantially retains its expressed biological activity.

A "target cell" refers to a cell intended for poration using a microfluidic poration device as described herein.

A "population" in reference to cells refers to a plurality of cells in one physical location, e.g. a culture dish, a centrifuge tube, a white blood cell population isolated from whole blood, etc.

As used herein, "transfection" refers to the process of deliberately introducing a foreign molecule through the plasma membrane and into a cell. Foreign molecules include but are not limited to genetic material, such as supercoiled plasmid DNA or siRNA constructs, proteins, such as peptides, antibodies, etc.

BRIEF DESCRIPTION OF THE DRAWINGS

FIGS. 2A-B is an illustration showing an exemplary microfluidic poration device (10), wherein a fluid containing cells inters the device through Inlet (14) into a channel space having sides (21) moving through a channel (20) comprising a nanostructure capable of piercing a hole in a cell in order to porate it, then flows out of the device through outlet (16). Aperture (23), open or partially/fully closed).

FIG. 2A illustrates a side view of one embodiment of a microfluidic poration device.

FIG. 2B illustrates an overview of one embodiment of a microfluidic poration device showing movement of one cell (light blue cytoplasm and dark blue nucleus) flowing through the device while simultaneously being squeezed and poked 2 times with a nanolancet (30) whose point is in the center of the channel prior to exiting the device.

FIGS. 3A-C is an illustration showing illustrations of nanoengineered surfaces in microfluidic poration device along with a depiction of a working mechanism of nanoengineered surface for precise intracellular delivery of a foreign molecule.

FIG. 3A demonstrates that only one cell can pass through each channel at a time, i.e. cells move through the channel one by one in single file, where the nanospikes will generate holes in the cell membrane. Sharp nanospikes with variable dimensions can be fabricated by standard microfabrication in a few steps.

FIG. 3B illustrates one embodiment where each channel is smaller than cell size to enable a hard contact between cell and nanospikes for one embodiment of a configuration of two nanospikes within each channel.

FIG. 3C shows SEM (scanning electronic microscope) images of nanolancets (left); and nanospikes in silicon, the nano tips of both lancet and spike can be less than 50 nm (right).

FIG. 9A-B shows exemplary images of microfluidic chip and the hardware unit used to flow the cells into the chip.

FIG. 9A shows a photograph of an exemplary microfluidic chip device (10).

FIG. 9B shows a photograph of an exemplary microfluidic chip device inside of an exemplary hardware unit (40) used to flow cells into, through, and out of the chip. Exemplary tubing for flowing fluids and cells into an inlet and out of the outlet of the device are shown (50).

DETAILED DESCRIPTION OF THE INVENTION

Figure 1:
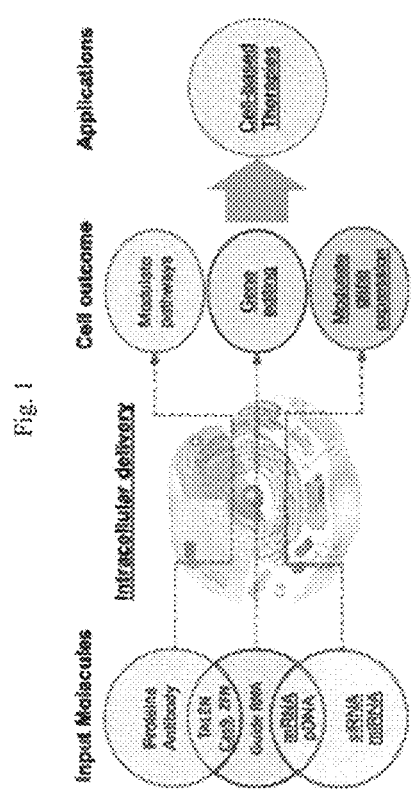
FIG. 1 is an illustration showing intracellular delivery of exemplary functional molecules such as nucleic acids and proteins to immune cells as one step in engineering cell functions for many subsequent embodiments of cell-based therapies, including but not limited to T cell based immunotherapy for cancer and B cell based autoimmune disease therapies.

The invention relates to a microfluidic poration device having a plurality of narrow channels, slightly smaller than the width of a target cell, wherein the channels are lined with a plurality of nanospikes in a row extending down the middle of the channel, i.e. in a row parallel to the sides of the channel. In one embodiment, one channel may have 2 nanospikes (or 2 nanolancets). Thus, in particular embodiments, the invention provides microfluidic poration devices capable of simultaneously squeezing cells while piercing holes in their membranes for allowing foreign molecules into cells. The holes in porated cells spontaneously close after exiting the channels, thus entrapping the foreign molecules inside of the target cells. This porated cell population is contemplated to have approximately a 95% viability with greater than 50% containing at least one foreign molecule.

Molecules diffuse into cytosolic space through a plasma membrane rupture (such as by poration). Poration refers to a type of rupture spontaneously repaired by cells within a few minutes of formation of a pore. It is contemplated that by controlling the size, number, and lifetime of open pores in a cell plasma membrane, this control would allow achievement of efficient intracellular delivery with precise dosage control for universal cell types and molecules. It is further contemplated that by constructing a microfluidic poration device as described herein, such a device would control the size and number of holes poked into one cell, in part for dosage control, i.e. number of foreign molecules entering the cell. Additionally, it is contemplated that such a device, as described herein, has embodiments for controlling the depth of the pore, i.e. by altering the length and/or width of the spike used to puncture the cell. In some embodiments, the depth of the pore is modified for delivering a foreign molecule to a specific part of a cell, e.g. cell membrane, cytoplasm, nucleus, etc.

I. Intracellular Delivery of Foreign Molecules into T Lymphocytes

In one embodiment, a method for intracellular delivery of foreign molecules into T lymphocytes is contemplated using a microfluidic poration device as described herein. It is not meant to limit the devices and methods to T cells. Indeed, a wide variety of cells are contemplated for use, including but not limited to other types of white blood cells, cancer cells, etc.

T cell-based adoptive cell therapy for cancer has demonstrated astonishing results and has multiple advantages over other cancer immunotherapies. One major factor limiting the success of adoptive cell therapy in humans is to identify cells that have the capability to target antigens selectively expressed on the surface of cancer cells and not on the normal ones. One solution is to introduce chimeric antigen receptors (CARs) into normal T cells to target cancer cells for therapy. The specificity of the T cells can be redirected by transfecting genes or adding genes (via gene editing) that encode CARs composed of a single chain antibody recognizing cancer-specific target (e.g., CD19 for acute lymphocytic leukemia (ALL)) and intracellular domains of CD3 and CD28 or others. While CAR-T cells work effectively for ALL, their success in solid tumors has been limited. One potential confounding factor in solid tumors is the immune suppressive tumor microenvironment that impairs T cell survival or causes T cell exhaustion. Thus, it would be beneficial to improve intracellular delivery of nucleic acid or protein or a combination of nucleic acid and protein (such as a CRISPR/Cas9 molecule-complex) to T cells in order to engineer/enhance their function for more efficient adoptive cell therapy.

Problems with current intracellular delivery to lymphocytes: Intracellular delivery to lymphocytes can be achieved by carrier or membrane disruption-based techniques. (i) Carriers package the cargo and protect from degradation, gain access to the intended intracellular compartment, and release the payload with the appropriate spatiotemporal dynamics. To date, viral vectors are the most widely used nucleic acid delivery agents for immune cells. Challenges such as immune response, cell activation, genotoxicity from viral vector insertion, limited number and size of genes, cost, quality control, and complexity of preparation, however, are concerns for viral vectors. Hundreds of non-viral vectors and synthetic carriers have been designed from vast combinations of lipid, polymer, and inorganic nanomaterials, often featuring functionalization with ligands, cell-penetrating peptides and other targeting or stabilizing agents. However, many of these carriers enter cells via the endocytic pathway and suffer from poor release, delayed unpacking, and carrier toxicity.

Moreover, target cells may not exhibit the appropriate receptors, surface interactions, endocytic activity, or endosomal escape pathways to render the carriers feasible for lymphocytes. (ii) Unlike carriers, membrane disruption-based approaches are less dependent on cargo properties and cell types, being able to deliver almost any submicron material dispersed in solution. The ability to rapidly switch membrane-perturbing effects on and off provides an additional level of control, enabling temporal manipulation and rapid, almost instantaneous delivery. Historically, some weaknesses of membrane disruption strategies have been: 1) inconsistent level of plasma membrane injury; 2) poor throughput or scalability (e.g. microinjection); and 3) inadequate understanding of plasma membrane disruption and recovery response. For instance, recently developed nanoneedle-based methods demonstrated potential for intracellular delivery, however, they rely on cell culture and adhesion on top of the nanoneedles to allow those nanoneedles penetrating into cells naturally, limiting the throughput, dosage control, efficiency, and cell types.

Existing technologies for intracellular delivery to primary immune cells, especially resting lymphocytes are limited by low efficiency and high toxicity. Recently nanostructure-based methods have demonstrated potential for effective gene transfection by penetrating DNA-loaded nanoneedles into the cell via gravity/centrifuge, or by electrophoresis through a nanostraw. However, those existing nanoneedle-based methods typically rely on cell growing and adhesion on the surface of nanostructures in order for the nanoneedles to penetrate into cells naturally, ending up with low throughput, time consuming, low precision of dosage control, or only work for adhesion cell types.

Therefore, a NanoEngineered Surface Technology (NEST) microfluidic poration platform was developed to overcome at least some of the issues in membrane disruption-based methods. As described herein, a NEST microfluidic poration device was developed and contemplated for intracellular delivery of one or more foreign molecules including but not limited to nucleic acids, proteins and other macromolecules simultaneously to a population immune cells at high efficiency, high throughput, with low toxicity to the target cells, at a fast rate and as a low cost method.

Fundamentally different from existing poration methods, in some embodiments disclosed herein, a membrane disruption based microfluidic approach porates cells by flowing cells in a pressurized fluid through narrow channels for simultaneously squeezing the cells for disrupting the cell membrane and forcing the cells over a specific number of nanostructures, such as a nanospike or a nanolancet, for piercing a uniform number of holes into each cell membrane flowing through the narrow channels.

In part, as a high throughput and low operation in view of time and low cost: we contemplate achieving a high throughput by flowing up to millions of cells through numerous, e.g. hundreds, of parallel microchannels within one minute in one chip. The side-by-side use of multiple chips can further increase throughput of porated cells. In one embodiment, the fluid within a fluidic poration device can be driven through simply by pipetting pressure, so both manufacturing and operation cost are low.

Further, the microfluidic poration device has a high poration (thus a high transformation) efficiency for delivering a precise dosage with low toxicity to the porated cells. By controlling the nanostructure geometry (such as sharpness and dimension of nanostructures for piercing holes into cells) and their interaction with cells flowing through (such as channel diameter (e.g. height, width, shape, etc. and flow speed), we are able to control the cell disruption/permeability for delivery locally at cell membrane, thus achieving precise intracellular delivery dosage and balance between cell viability/damage and delivery.

Moreover, such microfluidic poration devices as described herein may be used for ex vivo intracellular delivery to cells, such as immune cells for use in experiments for studying cell differentiation and function, and for use in cell based therapies. See nonlimiting examples in FIG. 1. In one embodiment, embodiments of inventive poration device operate under continues flow condition for ex vivo applications such as immune cell transfection. In one embodiment, a NEST microfluidic poration system is contemplated for use by flowing immune cells through the system for use in patient treatment, including an intracellular delivery of a foreign molecule followed by the treated cells being directly injected back (or flowed into via an intravenous (IV) tube) into the same patient as the source of the treated cells as part of a therapeutic treatment.

Additionally, the present invention contemplates bridging a gap between understanding cell membrane disruption and intracellular delivery by quantitatively characterizing cell membrane permeability and repair at molecular level and cellular level in response to mechanical disruption. So far, biologists have not applied the fundamental insights gleaned from membrane disruption and repair studies towards engineering cell permeability. As described herein, studies based upon embodiments of a microfluidic poration device as described herein for bridging the scientific gap between two disparate fields, first, the engineering of intracellular delivery approaches; and second, the cell biology of plasma membrane disruption and repair response.

II. Creating a Microfluidic Platform for Intracellular Delivery of Molecules.

In one embodiment, when transfecting a cell by poration, the cell membrane is disrupted in a controllable manner for allowing efficient diffusion of functional (foreign) molecules, in the surrounding solution, into the cytosolic space. Further, by localizing the disruption to a small area of the plasma membrane without damaging other areas of the plasma membrane or intracellular components of cells may minimize toxicity from such membrane disruption process. Although researchers showed that mechanically deforming cells (squeezing) generates transient pores in the cell membrane, allowing influx (diffusion) for intracellular delivery of some types of molecules without inducing significant toxicity to cells, the parameters for successful transfection would induce toxicity effects. As one example, for an efficient intracellular delivery in this reference's cell squeezing based approach, it was estimated that cells need to be deformed by more than 60% when flowing through a constriction (width of smaller than 40% of cell diameter). While these squeezing parameters might work on some cells, such intense cell deformation is challenging for other types of cells, such as immune cells, i.e. white blood cells, lymphocytes, etc., particularly for cells whose nucleus fills almost the whole cytosolic space. For these types of cells intense nucleus deformation caused by this type of cell squeezing is likely to at least cause severe DNA damage. Moreover, as both the plasma membrane and the nuclear envelope rupture, these cells are more likely to die.

In contrast, herein is disclosed a new strategy to avoid toxicity to cells whose nucleus may be damaged by extreme cell squeezing while maintaining high percentage of delivery efficiency and high throughput for large cell populations. In part, by designing embodiments of microfluidic poration devices which combine a controlled level of cell squeezing to avoid irreversible damage to constricted cells, with a defined placement, piercing depth, and number of nanostructures for piercing holes would provide high percentages of transformed cells along with high percentages of viability. Thus, in preferred embodiments, integrating a limited (defined) number of nanostructures, such as nanospikes, nanolancets, etc., on the surface of channels within microfluidic channels, and sizing the channels in relation to the size and types of cells flowing through the channels, for the entire population of cells of about the same size and type flowed through the same embodiment of a poration device, the plasma membrane will be disrupted to the same degree in a precise manner with minimum toxicity, leading to the diffusion of surrounding molecules of interest (i.e. foreign molecules) into cytosol (cytoplasm) a process also called transfection.

III. Embodiments of NEST Microfluidic Poration Devices.

Described herein are embodiments of a microfluidic poration device capable of pressurized fluid through-flow for inducing repairable poration of target cells within the fluid.

A. Methods of Flowing Cells Though A Microfluidic Poration Device.

Exemplary methods are contemplated for use in flowing cells through a microfluidic poration device as described herein. Merely for nonlimiting examples, the following embodiments are described. In one embodiment, cells may be pulled into a syringe by hand then gently pushed through the device by hand, collecting the cells exiting the device into a sterile collection device, such as a centrifuge tube, a cell culture tube, an Eppendorf tube, etc. In one embodiment, cells may be pulled into a syringe by hand then gently pushed through the device by hand. In one embodiment, cells may be loaded into a device capable of automatically pumping fluid through the device. It is not meant to limit the type of device or method for selecting a target cell population, then loading and flowing target cells through a microfluidic poration device. In some embodiments, flowing a cell through channels allows the cell to essentially roll through the channels thus rolling over the nanostructures. In some embodiments, flowing a cell through channels is achieved by using pressurized fluid essentially pushing cells through the channels but not substantially damaging the cell membrane. In some embodiments, whether the target cells are rolling or being pushed, the cells are being simultaneously squeezed while moving through a channel whose diameter is small enough to compress the cell on two or more sides, yet without damaging the cell, i.e. without causing a loss in viability merely by moving the cell through the channel.

As cells are moved through the channels by pressurized fluid, their plasma membrane is distorted in order to fit through the channels while the nanospikes poke holes through the distorted membrane and through the submembrane architecture in order to allow molecules in the flow media to enter the porated cell. Upon exit from the channels the disrupted plasma membrane and associated architecture returns to its previous morphology.

B. Target Cells

In some embodiments, a target cell population is provided by sorting cells with one or more selected physical characteristic (e.g. size), morphological characteristic (e.g. granularity), nontagged cells sorted from a tagged cell population, e.g. antibody, or tagged cells sorted from a nontagged cell population by flow cytometry for providing a target cell population. In some embodiments, a target cell population selected and sorted by flow cytometry is collected then flowed through a microfluidic poration device.

In other embodiments, a target cell population selected and sorted by flow cytometry is flowed directly into a microfluidic poration device through fluidic connections. In some embodiments, a target cell population may be obtained by collecting a blood sample from a donor patient followed by flowing a blood sample comprising white blood cells into a microfluidic poration device.

In some embodiments, after white blood cells are porated for incorporation of a foreign molecule, the white blood cells are then collected for infusing back into the same donor patient as part of a treatment.

1. Engineering Immune Cells by Intracellular Delivery of a Foreign Molecule

T cell-based adoptive cell therapy for cancer has demonstrated astonishing results, however its success in solid tumors has been limited. One potential confounding factor in solid tumors is the immune suppressive tumor microenvironment that impairs T cell survival or causes T cell exhaustion. In one contemplated embodiment, a microfluidic poration devices as described herein may be used for intracellular delivery of nucleic acids into T lymphocytes for modulating cellular functions of the transfected T lymphocytes. In some embodiments, gene of interest may be inserted for study in primary lymphocytes for identifying specific functions of that gene.

Previous studies showed that CAR-T cells that express a cytokine IL-7 are more effective at killing tumor cells. IL-7 may also support T cell survival. Thus, merely as one contemplated application, e.g. using an embodiment of a microfluidic poration device described herein for enhancing the expression of IL-7 cytokine in primary T cells by intracellular delivery of an expression plasmid encoding or mRNA expressing IL-7 into porated T cells. Primary T cells can be isolated from several sources, including but not limited to mouse spleen, human blood samples, etc. Further, populations of white blood cells may be obtained commercially, for example, Bonfils Blood Center (now Vitalant), Denver, Colorado. After poration, engineered T cells will be cultured for 3-4 days, then examined for survival using flow cytometry or western blotting for cleaved Caspase 3, an apoptosis marker.

As a contemplated result, a much higher percentage of T cells will remain alive over time in the engineered group than control group, i.e. T cells porated but without an IL-17 nucleic acid. These types of studies will allow us to develop a better approach to deliver IL-7 into primary T cells. It is possible that DNA plasmid expressing IL-7 may not be effectively delivered into T cells since the physical size of DNA plasmid in relaxed form in the solution can be a few hundreds of nm or even a few um, making it low efficient in diffusion into cell. In this case, we may use mRNA that is much smaller than DNA plasmid.

In one contemplated embodiment for enhancing gene delivery into T cells, DNA or mRNA are intended as foreign molecules to incorporate into porated cells are first pretreated the with nanoparticles, such as commercially available lipofection kit (e.g. Lipofectamine 2000), in which liposome can fold and compress nucleic acid molecules into a lipid nanoparticles with a size of smaller than 100 nm, depending on the parameters of the nucleic acid. Thus, an alternative is to add a step of pretreating the DNA (or mRNA) with nanoparticles, such as Lipofectamine 2000. Although it is not necessary to understand the mechanism of an invention, it is believed that using a smaller size foreign molecule, i.e. nanoparticles, enhances gene delivery into T cells during poration.

2. Use of Engineered T Cells.

Such modified T cells are contemplated for use in treating immune disorders, such as for primary immunodeficiency disease, PID(D)). Another contemplated application for T cell modification using a device described herein as part of an adoptive cell transfer therapy for killing cancer cells by engineering T cells to more efficiently kill specific types of cancer cells.

C. Examples of Channel Configuration.

As described herein, a NEST (NanoEngineered Surface Technology) microfluidic poration device is provided comprising nanostructures, such as nanospikes, nanolancets, as a structured surface for precise plasma membrane disruption as part of a nanoengineered surface system for precise intracellular delivery of foreign molecules.

Specifically, a series of nanospikes was fabricated on the surface of the substrate within each microfluidic channels for testing. Each device consists of up to hundreds of channels for high throughput purpose (FIG. 3a).

Each channel is configured to restrict the number of target cells entering the channel to one-target cells at a time so that target cells move through the channels in a single file. Thus, in one embodiment, a channel is configured to be the same size as or smaller than the diameter of a cell to restrict the number of entering cells to one, so that cells flowing through the channel do so in single file. Such configuration also provides a hard contact between each target cell and points of the nanostructures.

Thus the configuration of a channel may be matched to the diameter, size and structure of a cell, such as a rigid cell. e.g. an immature lymphocyte, a flowable cell. e.g. an mature macrophage, etc. As each cell is passing through the channel the nanostructures located therein will generate a hole at least into the plasma membrane. When desirable, the dimensions of the nanostructures may be configured to additionally poke a hole through the plasma membrane and additionally through the nuclear membrane. An example as one embodiments of a device showing nanospikes relative to channel width, channel height and cell size, are shown in FIG. 2B and FIG. 3A-C. The geometry and dimension of the nanostructure, such as height, width, angle of point, sharpness is contemplated for configuration for correlating operating parameter values and cell membrane permeability. One exemplary means to control the cell membrane disruption is to control the quantity and size of holes at plasma membrane punctured by the nanostructure.

The number and size of pores may also determined by the number and geometry of nanospikes fabricated in each channel. The size of nanospike can be from 50 nm to sub-micron, much smaller than a microinjection needle. In one embodiment, the device comprises channels fluidically connected in parallel. In one embodiment, the device comprises channels fluidically connected in series. In some embodiments, the device comprises channels fluidically connected in parallel and in series.

In one embodiment, the device comprises channels having diameters slightly smaller than the width of the target cell, wherein the channels are lined with a plurality of nanostructures (nanospikes/nanolancets) located in the center of the channels. In one embodiment, the number of nanostructures is 1 per channel. In one embodiment, the number of nanostructures is 2 per channel. It is not meant to limit the number of nanostructures as nanospikes or nanolancets per channel. Indeed, the number of nanostructures per channel may range from 1-50, preferably up to 2 per channel, up to 4 per channel, up to 6 per channel, up to 8 per channel, up to 10 per channel, up to 12 per channel, up to 14 per channel, up to 16 per channel, up to 20 per channel or more, depending upon the size of and type of target cell intended to flow through the channel. In some embodiments, the number of nanostructures depends upon the length of the channel. In some embodiments, the diameter of the channel opening is slightly larger than the diameter of the target cell. Referring to a diameter of a cell, it is known that for a population of cells there may be an average diameter of a cell population because there is variably of diameters between cells of the same population. Thus, in some embodiments, a diameter of a channel may be selected from slightly larger, the same size or slightly smaller than the average diameter of a target cell population.

Thus, in some embodiments, the diameter of the channels within the same device are the same size and chosen to match the average diameter of the cells.

D. Nanostructures Having Points Extending into the Space of a Channel.

A balance between cell viability and intracellular delivery efficiency More nanospikes and larger spikes will generate more or bigger holes on the cell membrane, and lead to more delivery or cause lower cell viability. In order to ensure hard contact between cell and nanospikes, the width (e.g. W: 8 um-20 um) and height (e.g. H: 8 um-20 um) of each channel, in one embodiment, is slightly less than cell size, as shown in FIG. 2b. A lower channel height than the diameter of a target cell will squeeze cells leading to a standard pore size with the same disruption for each target cell. When compared to cells bouncing through a large channel with random contact with a nanostructure, cells moving through a channel while being squeezed onto the nanostructures have larger pores with more membrane disruption.

It is not meant to limit the number of nanospikes or nanolancets used in any one channel. In fact, any desired number of nanospikes can be fabricated. The number and size of pores for each device embodiment may be determined by the number and geometry of nanospikes fabricated in each channel.

FIGS. 3a and 3b shows the nanolancet and nanospikes on the surface of silicon substrate fabricated by the combination of DRIE and RIE, the tip is less than 50 nm, sharp enough to rupture cells. SEM is used to image and measure the dimension of fabricated nanostructures and compared to designed values. Nanospike and nanolancet with variety of aspect ratio and sharpness are fabricated for test.

In one embodiment, the present invention contemplates a device comprising a plurality of channels, wherein each channel has a different number of nanostructures in a row down the middle of the channel with relative channel diameters sized to a specific target cell population. Although it is not necessary to understand the mechanism of an invention, it is believed that this device maximizes both cell viability and intracellular delivery efficiency.

Figure 5:
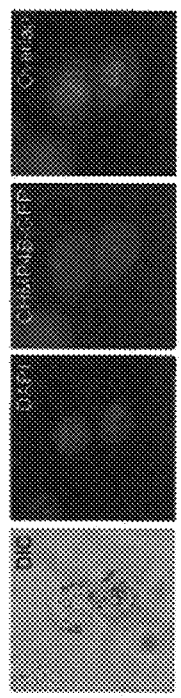
FIG. 5 shows differential interference contrast (DIC) and immunofluorescence microscope images demonstrates a typical image 1-5 minutes after membrane disruption by a microinjection needle whose tip is typically 1-3 um. GFP labeled CHMP4B is recruited to wounding site to repair membrane rupture and disappear in 6-15 minutes when repair is done.
Figure 6:
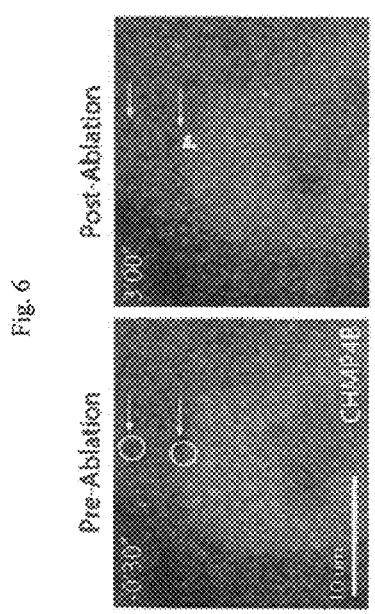
FIG. 6 shows microscopic images of localizing membrane disruption with fluorescence microscope images. Representative images of a HeLa cell expressing CHMP4B-EGFP before and after UV laser wounding at the plasma membrane. Localized enhancement of CHMP4B-GFP was observed at laser wounding sites indicated by arrows.
Figure 7:
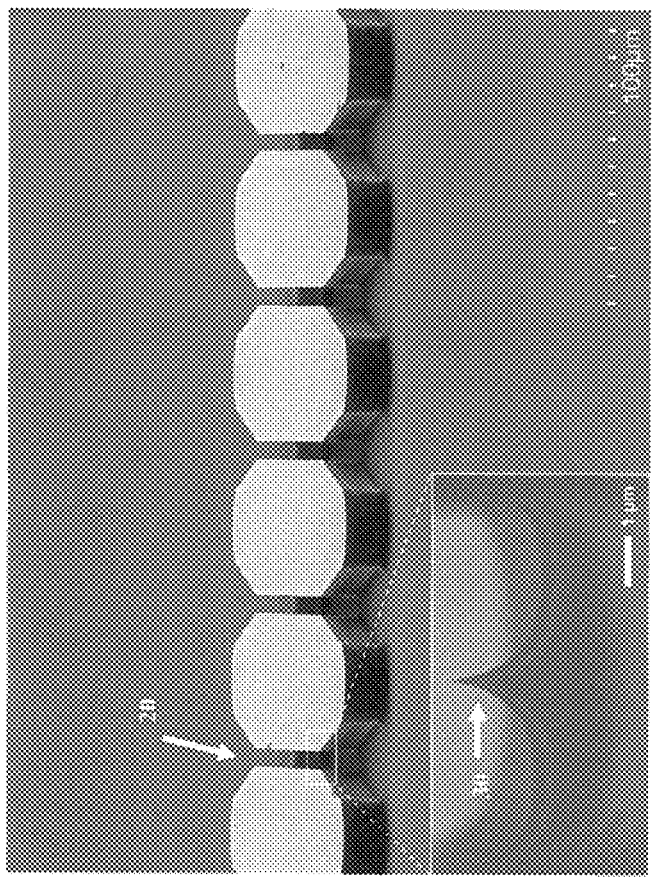
FIG. 7 shows exemplary scanning electron microscope (SEM) images of an array of subchannels containing nanospikes. Two nanolancets (30) are positioned in the center of each subchannel (20) in single file, i.e. parallel to the sides of the subchannel. Although the top side of the channel is not present for this image, the subchannel in the device has an upper side for encasing the cells moving through the subchannels.
Figure 8:
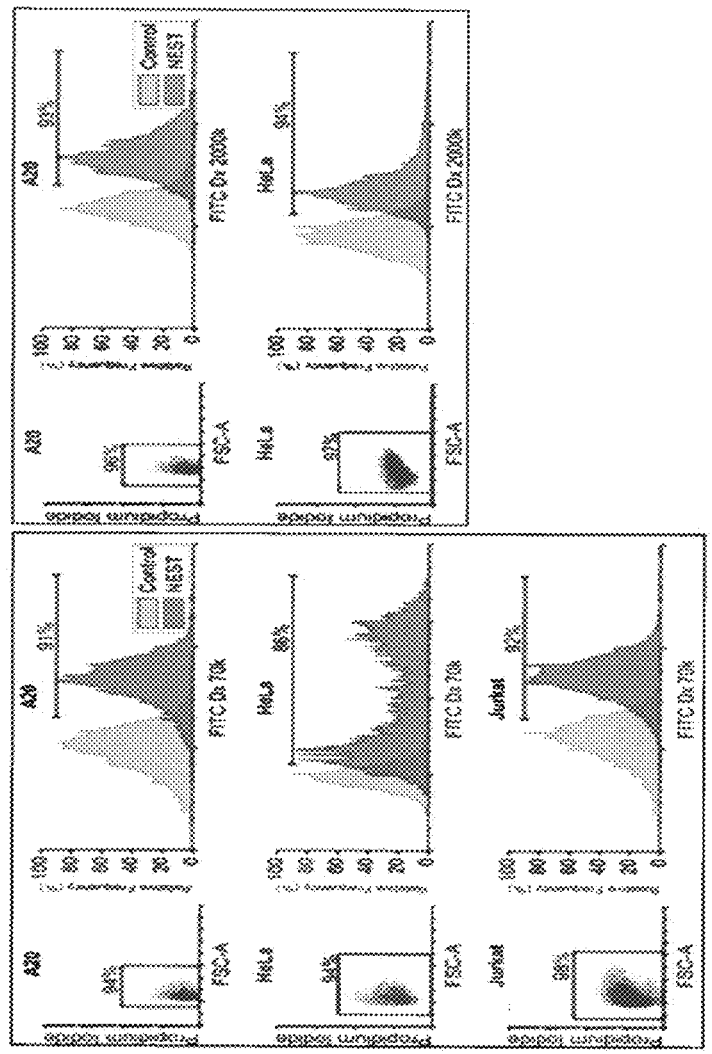
FIG. 8 shows exemplary fluorescence intensity histogram from flow cytometry of human epithelial cell line (HeLa), murine B cell line (A20) and human T cell line (Jurkat) treated by a NEST device, as shown in FIG. 7. Green histogram illustrate the delivery of fluorescence labeled molecules namely FITC 2000k Dextran or FITC 70k Dextran. Superimposed gray plot depicts the control sample where the cells are exposed to the aforementioned molecules at the same amount of time as the cells treated by NEST. The gating region is set to account 5-10% of fluorescence to compensate autofluorescence, surface binding, and endocytosis. Cell viability is determined by propidium exclusion that the gating region is determined from control sample with no addition of propidium iodide.

Preliminary results in FIG. 5 show that cells can recover from membrane disruption (pore) by a microinjection needle with a tip of about 2 um. CHMP4B is a protein than involves in cell membrane repair. Three minutes after cell membrane penetration by a microneedle, Green fluorescent protein (GFP) tagged chromatin-modifying protein/charged multi-vesicular body protein (CHMP) aggregates were observed at the rupture site, meaning cell is repairing the membrane. Those CHMP4B-GFP aggregates disappear after 6-15 minutes, indicating repair is done. So it is contemplated that high viability is achieved using the presently disclosed NEST device described herein, since the size of nanospike can be from 50 nm to sub-micron, much smaller than microinjection needle.

Example A—Device Fabrication

Because of the fast-growing nanotechnology, there are many ways to fabricate those nanostructures. A typical and standard fabrication procedure is shown in FIG. 2a. After standard photolithography step, modified silicon dry etching is used to form these nano tips in silicon substrate. By using a combination of anisotropic DRIE (deep reactive ionic etching) and isotropic RIE (reactive ionic) etching, we have more flexibility to control the aspect ratio of these nanostructures. Finally, PDMS (Polydimethylsiloxane) microfluidic channels are fabricated using soft lithography and bounded to the silicon substrate to seal the channels as a final device. PDMS is a biocompatible silicon-based organic polymer and has been widely used in many fields including lab on a chip and microfluidics.

Anticipated outcomes and alternative strategies: we expect to design and develop a fabrication process for the proposed NEST microfluidic devices with a variety of nanostructures, such as nanospikes and nanolancet, within microfluidic channels. We expect that a wide range of high aspect ratio and sharpness of the nanolancet and nanospike will be achieved to control the cell membrane permeability. Based on our preliminary results in FIG. 4, we don't anticipate problems in fabricating these NEST devices. However it is possible that the very sharp nanospike tips might break while cells are flowing through. In this case, we will (1) increase the foot size of each nanospike meanwhile lower the channel height, (2) reduce the flow speed, and (3) if needed, to replace nanospikes with nanolancet which is more robust. It is possible that the PDMS is too soft to push the cells against the nanostructure while they flowing through the channel, we will use Pyrex glass to form the microfluidic channel via anodic bonding.

Example B—Validating the Microfluidic Platform for Intracellular Delivery

We tested one embodiment of a microfluidic poration device having two nanospikes using Hela cells and fluorescent Dextran (cascade blue) with molecular weight of 3K Dalton.

As one example described herein, 3 KDa fluorescent Dextrans were delivered into ~50% of cells with ~95% viability, achieved using one embodiment of a poration device described herein, having 2 nanospikes in each channel, See, FIG. 2B and FIG. 3A-B.

Figure 4:
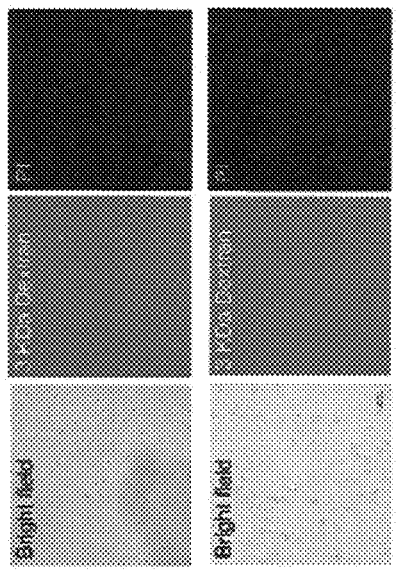
FIG. 4 shows microscopic bright field images of Hela cells treated using the 2-spike NEST device are imaged and analyzed, 3 KDa fluorescent Dextrans are delivered into ~50% of cells with approximately 95% viability (upper panels), almost no damage was observed compared with negative control—(lower panels).

PI (propidium iodide) was used to measure cell viability. As shown in FIG. 4, our preliminary results indicate that a delivery of ~50% with a viability of ~95% are achieved using the nanospike device (with 2 nanospikes in each channel). In this experiment, cells are first mixed with 3 KDa dextrans before flowing through the device.

After treatment, we kept the cells in the incubator for 3-5 minutes to allow them to recover, then wash cells with new medium and add PI (cell viability indicator) before imaging using fluorescent microscopy. We contemplate testing with other size dextrans, nucleic acids, and proteins.

Rationale: the delivery performance of the proposed membrane-disruption based NEST microfluidic platform may be dependent on the size and number of pores at cell membrane, plus their lifetime.

Example C—Cell Membrane Disruption and Reseal by NEST Device

In some embodiments, a NEST device will be used to characterize and understand cell membrane disruption and repair dynamics after poration of the target cells. One strategy to characterize membrane disruption and repair in live cells is to track localization of fluorescently tagged proteins that are recruited to repair plasma membrane wounds. These include ESCRT (endosomal sorting complex required for transport) subunits, various annexins, and MG53. Fluorescent molecules and GFP mRNA or pDNA will be used to measure the efficiency of intracellular delivery using flow cytometry. Those characterization will be correlated to the nanostructure properties and other systematic parameters to optimize and improve the NEST system.

The cell membrane repair literature has defined lists of genes and proteins involved in plasma membrane repair and cell stress response. However these studies are beyond the scope of our proposed work. In this sub aim we will focus on the quantification of cell membrane disruption that are immediately related to intracellular delivery, so the size, number and reseal kinetics (lifetime) of the disrupted pores will be quantified.

Recently researchers have demonstrated the use of fluorescent-tagged ESCRT-III subunits to monitor cell membrane disruption and repair dynamics. HeLa cells stably expressing GFP-tagged CHMP4B at endogenous levels, a subunit of the ESCRT-1 complex, were used to monitor and measure the membrane dynamics after cell membrane was disrupted by physical and/or chemical approaches, as shown in FIG. 4 where CHMP4B-GFP was recruited to the wounding sites on plasma membrane.

Our preliminary results in FIG. 5 also shows similar phenomenon: CHMP4B-GFP was recruited to the wounding site generated by microneedle within a few minutes. We will use the same assay and cell line to monitor and measure the membrane disruption dynamics, including size, numbers and lifetime of those disrupted pores generated by our proposed NEST. As a backup strategy, antibodies added to the extracellular solution can also be used to label specific proteins involved in membrane repair. For the next steps, the cells treated by the NEST device will be imaged by high-resolution confocal and structured illumination microscopes available for shared use on campus. Given the amenable resolution (~125 nm) of advanced structured illumination microscopy, this strategy is anticipated to yield improved insights into the number, distribution and dynamics of plasma membrane disruptions generated by a given treatment.

Example D—Characterization of Delivery Performance

In some embodiments, we will test the delivery performance of nanospike based NEST in terms of delivery efficiency, cell viability, and throughput. Initial tests will be implemented with dye-conjugated dextrans, which are either neutral or slightly negatively charged to serve as a low-cost, reliable, and inert markers.

Commercially available 70 kDa dextrans suitably represents the average size range of proteins of interest and have been verified to be approximately 7-12 nm with dynamic light scattering measurements. Cells will be mixed with those markers before treatment and incubated for a few minutes after treatment. Treated cells will be washed to remove those molecule markers and mixed with PI (propidium iodide, to indicate cell viability) for quantitative analysis. Standard flow cytometry analyzer will be used to analyze the delivery performance for several cell types from immune cell line to primary lymphocytes, including A20, Jurkat cells, primary human T cells, mouse T cells, etc. To complement flow cytometry-based fluorescent readouts, intracellular distribution will be post-checked with confocal microscopy. Gene transfection, including GFP DNA plasmid and GFP mRNA, will also be tested on primary T cells to further exam the delivery performance.
Molecule Influx (Intracellular Delivery).

We will use flow cytometry to analyze quantitatively intracellular delivery of fluorescently labeled molecules, such as fluorescein (FITC) conjugated dextrans and beads, to measure the size and life time of cell membrane disruption. To determine the size of membrane disruptions, fluorescent beads, commercially available in sizes starting from 10 nm, will be added to the extracellular solution.

The ability of cells to reseal their membranes after a certain number of minutes will be tested by adding propidium iodide (PI) before flow cytometry. Cells that are unable to reseal will be identified by strong red fluorescence as PI diffuses into the cell and increases its fluorescence upon binding to nucleic acids. Alternatively, the membrane reseal kinetics can be measured by analyzing the intracellular concentration of influx Dextrans at specified time points, similar strategy to reference [37].
Molecule Efflux.

The cytosolic molecules may flow out to extracellular space when there is a pore at plasma membrane. Too much efflux of cytosolic molecules may cause damage to cell as well. We will use flow cytometry to analyze quantitatively molecule efflux. We will first deliver fluorescently labeled molecules, such as fluorescein (FITC) conjugated Dextran, to cells using NEST device or other methods such commercial electroporation and divide into two groups. Group A is used to measure the fluorescent intensity using flow cytometry. Group B will be treated again by the NEST device and measured using flow cytometry. The fluorescent intensity of these two group will tell us quantitative molecule efflux from the cytosolic space. We will also test a variety of molecular weight Dextrans to mimic different size molecules in the cell.

Example E—Method of Poration Using a Microfluidic Poration Device

As one example, a volume of 200 μL sample, with an exemplary cell concentration of 2 M/mL in a fluid, will be flowed through the device for each run, the remaining volume in the device and connecting tubing is estimated around 50 μL, so effluent collection of porated cells is estimated around 150 μL of sample with approximately 300K cells in each run of cells through the device. Four groups of control experiments will be carried out: (1) cells mixed without fluorescent markers and without treatment. (2) cells mixed with fluorescent markers without treatment, (3) cells with fluorescent marker treated by microfluidic channel without nanostructures, (4) cells without fluorescent marker treated by NEST microfluidic device.

In some embodiments, exemplary working buffer, i.e. a fluid containing cells and foreign molecules, includes PBS and culture medium for use with cell treatments, i.e. poration, in a NEST device as described herein. In some embodiments, exemplary flow rates of 10, 20, 50, and 100 L/min are used.

In some embodiments, exemplary foreign molecules contemplated for delivery include but are not limited to fluorescent Dextran of 3, 70, and 150 KDa, in addition to proteins, lipids, nucleic acids, etc. Exemplary molecular concentration in the cell sample solution ranges from 1 μg/mL-1 mg/mL (e.g. 1, 10, 100, and 1000 μg/mL, respectively). Each condition will be repeated (at the same sample size) for 3-5 times to measure (average±SD) the delivery efficiency, average fluorescent intensity, and viability using flow cytometry. For GFP DNA and GFP mRNA delivery tests, cells, such as Hela cells, cultured in 3 different flask will be harvested, washed with PBS, and mixed with GFP DNA or mRNA in a poration fluid, right before a poration device treatment.

Exemplary determination of poration efficiently and cell viability may be determined after treatment by washing cells with new (fresh) buffer medium to remove the GFP DNA or mRNA then culturing in an incubator for 24 hours. When a florescent marker is used, such as GFP, flow cytometry will be used to measure the florescent. GFP, expression and viability of the treated cells. For an exemplary cell membrane repair analysis, a construct such as GFP-CHMP4B may be used. Then cells will be imaged after in certain time course (e.g. 30 seconds (s), 1, 3, 5, 10, 15, and 30 mins) after treatment by the NEST device, and analyzed for the number and size of the GFP-CHMP4B foci, which will indicate the information and dynamics of cell membrane rupture and repair.

Exemplary sample size (i.e. a population of cells for each condition) will be at least n=10.

Additional contemplated experiments include comparing NEST (poration devices described herein) with commercial electroporation devices and lipofection methods.

In a further contemplated embodiment, a NEST device may be used in combination with lipofection components.

Example F—Comparison with Other Methods

We contemplate comparing our NEST device with commercial transfection methods including NEON electroporation and lipofection in delivery of dextrans and GFP DNA/RNA. Anticipated outcomes and alternative strategies are also described herein. The basic hypothesis of this proposal is that cell membrane permeability can be controlled by mechanical disruption using nanostructures. We expect to characterize how cell membrane is disrupted by sharp nanospikes at flow condition, and quantitatively understand cell response (repair) to such mechanical disruption at cellular level and molecular level. We also expect to develop a quantitative correlation between cell delivery efficiency, cell death, membrane disruption, and nanostructure properties, to help answer questions such as number and size of pores, which matters more?

A potential pitfall could be ineffective membrane disruption by the nanospikes. (1) It may be possible that cells may just flow across over these nanostructures without being disrupted. In this case, we will further decrease the channel height and width to squeeze the cells at a level to ensure that those sharp nano tips could physically contact cells and puncture or scratch the cell membrane successfully. (2) We may also use hypertonic buffer (with lower osmolality than cells) to swell the cell volume, which would enhance the membrane disruption.

V. Advantages of Using NEST Microfluidic Poration Devices Over Other Types of Poration Devices.

There are numerous other types of microfluidic devices described in the literature, however the microfluidic poration device provided herein has numerous advantages and additional benefits over those previously described in publications. In fact, microfluidic devices described in publications a different from the device described herein, the following are some examples.

A microfluidic device is described comprising a plurality of flow channels arranged in parallel with perturbation features for constricting one or more cells and piercing cells with one or more spikes, e.g. nanospikes, microspikes, nanoteeth, etc., to induce temporary holes in the cell membrane for intracellular delivery of a compound suspended in solution with the cells, in WO2017173373A1. "Flow-through microfluidic methods and devices featuring membrane-perturbing surface interactions for intracellular delivery." To Stewart, Langer, Jensen, and Ding, published 5 Oct. 2017. Moreover, this reference describes channels with at least one spike for piercing a hole in the cell membrane. However, there is no specific written description of the location of the one (or more) spikes located relative to the configuration of the channel, where channels may be a circle, an ellipse, an elongated slit, a rectangle, a square, a hexagon, and a triangle, etc. Because spikes shown in the figures of WO2017173373A1 are located in a row across the width of a rectangular channel, they include spikes in the middle of the channel along with additional spikes extending to the edges of the rectangular channel. However, there is no specific description of one or more spikes restricted to the middle area of a channel. In fact, specifically for the presence of 1 or 2 or more spikes, there is no indication where these spikes would be located in the channel. Furthermore there is no written description or drawing of 1 spike in the middle of the channel, or more than 1 spike extending in a row parallel to the sides of the channel.

Even further, there is no exact size of a "spike" provided in the written description of the WO2017173373A1 reference, other than general statements to perturbations: "at least 0.1 nm . . . at least 1 nm . . . between about 5 to about 20 nm . . . ." and "sufficient in size and/or number to allow for the intracellular delivery of a payload, but do not result in a substantial loss of cell viability." [0062]. FIGS. 9A and 9B, of WO2017173373A1, show images of solid spikes approximately 3 um across with an approximate 200 nm point. Additionally, the image of a spike in FIGS. 9A and 9B, of WO2017173373A1, appears to be similar to the image of a nanolancet as described herein. The sizes of nanospikes inferred from these images, along with the written descriptions including sizes of nanospikes ranging from 50 nm to sub-micron. However, even though some of the sizes of the nanostructures spikes may appear to be similar. Further, the nanospike/nanolancet may be distributed randomly on the surface of the channel in this publication, further cells pass though randomly across those nanostructures. Thus, leading to cells randomly poked by nanospikes, having uneven membrane rupture and uncontrollable dosage of delivery. In contrast, it is contemplated that by using a device and methods described herein, delivery to porated cells will be the same dose of drug and molecules into each cell moving through the inventive device. In fact, unlike as described in the referenced publication, the channel sizes described herein for the inventive poration device, positions each cell over a nanospike/lancet in the same position, i.e. in the center of the channel, as it moves through the channel for precise dosage control.

Size of the channel: The reference describes the channel as: "[t]he cross-sectional geometry of the microfluidic flow channel comprises at least one cross-sectional channel dimension that permits the one or more cells suspended in the solution to pass through the microfluidic flow channel . . . the cross-sectional channel dimension of the microfluidic flow channel is selected to increase interactions between the cell and the perturbation features." [0015] and "[s]uch that the cells experience constriction as they flow through the microfluidic flow channel . . . , constriction is not primarily to deform the cells but to force the cells into contact with perturbation features on the membrane perturbing surfaces." [0055] However, there is no explicit description of configuring the channel opening to restrict cells to flowing through the channel in single file.

In fact, although figures in this application show a dotted circle representing a single cell in the middle area of the channel being constricted by the narrow height of the opening, the channel shown is much wider than the represented cell. Further, there is no explicit description of restricting the flow of a cell to the middle of a wide channel, nor a channel that restricts the entry of cells to one at a time, much less cells flowing in single file through a channel. So it appears that the cross-sectional geometry of the channel described in this publication does not restrict cells to flowing through the channel in a single file but instead, as described in the publication, allows more than one cell into the channel at the same time.

Compounds for intracellular delivery include a gene editing system such as TALENs. CRISPR/Cas9, and zinc-finger nucleases; proteins, small molecules, nucleic acids (e.g. shRNA-encoding sequence; siRNA; RNA and/or DNA), polynucleotides, modified polynucleotides, nucleoproteins, lipids, carbohydrates, macromolecules, vitamins, polymers, fluorescent dyes and fluorophores, carbon nanotubes, quantum dots, expression vectors, nanoparticles, steroids, and biologic, synthetic, organic, or inorganic molecules or polymers thereof.

Examples of cells include T cells, prokaryotic cells, mammalian cell such as a stem cell (e.g., embryonic stem cells, induced pluripotent stem cells (iPSCs) and the like), a red blood cell, a white blood cell or a cell derived from any mammalian tissue.

Such cells comprising compounds may be used as therapeutics, such as for gene therapy and adoptive T cell transfer.

Although this reference describes a microfluidic device for porating cells moving through a channel by simultaneously squeezing and piercing the cells for delivering a compound to the cell, this reference does not explicitly describe flowing cells in single file through the channel where the location of spikes is restricted to the center area of a channel. Further, there is no explicit mention of using just two spikes per channel.

Another example of a device is described in Xiaoyun Ding, Sharei, et al., WO/2016/077761. "Disruption and field enabled delivery of compounds and compositions." App.— Filed Nov. 13, 2015—Published May 19, 2016—Massachusetts Institute Of Technology. This reference describes a microfluidic system for generating holes in a single cell's plasma membrane for intracellular delivery of compounds to a cell. The device has channels for simultaneously constricting cells flowing in single file, i.e. one cell at a time, through the channel while moving through an electric field for prorating the cell. Treated cells may be used for drug screening, dosage studies and as a therapeutic. Cells and applications include circulating blood cells (e.g. lymphocytes), high throughput delivery of sugars into cells to improve cryopreservation of cells, especially oocytes, targeted cell differentiation by introducing proteins, mRNA. DNA and/or growth factors, delivery of genetic or protein material to induce cell reprogramming to produce iPS cells, delivery of DNA and/or recombination enzymes into embryonic stem cells for the development of transgenic stem cell lines, delivery of DNA and/or recombination enzymes into zygotes for the development of transgenic organisms, DC cell activation, iPSC generation, and stem cell differentiation, nano particle delivery for diagnostics and/or mechanic studies as well as introduction of quantum dots. Skin cells used in connection with plastic surgery are also modified using the devices and method described herein.

Although this reference a microfluidic device for porating cells moving in single file through a channel while being simultaneously being constricted and exposed to an electrical field, this reference does not explicitly describe poration of cells flowing in single file through a channel while being simultaneously squeezed and poked by nanospikes for intracellular delivery of a compound.

Other examples of devices are described in Stewart. Sharei, Xiaoyun Ding, et al., Jensen, "In vitro and ex vivo strategies for intracellular delivery." Nature Review. 538: 183-192 (2016). This review reference describes membrane disruption for intracellular delivery of cargos, e.g. proteins, nucleic acids, etc., aided by nanotechnology, nanoneedles and microfluidics, including by cargo diffusion from the extracellular medium through holes after withdrawal of the needles. Box 1 describes microfluidic versions including cell squeezing and nanoneedles. In a different location in the reference nanoneedles are described as capable of penetrating the cell membrane for allowing a compound to enter the cells, such as delivery of siRNA, peptides, DNA, proteins, and impermeable inhibitors to challenging cell types such as neurons and immune cells. Additionally, FIG. 4 shows single cells moving through channel constrictions for cell squeezing and other cells poked with nanostraws for inserting molecular cargos. However, this reference does not describe a microfluidic poration device with a channel having spikes where cells flowing in single file are simultaneously squeezed and poked for intracellular delivery of a compound.

Another example of a device is described in Dong Huang, et al., "Continuous Vector-free Gene Transfer with a Novel Microfluidic Chip and Nanoneedle Array." Current Drug Delivery, 16:164-170, 2019. This reference describes a microfluidic device for porating cells by piercing holes into the membranes using a staggered nanoneedle microarray on one of the channel's internal surfaces at a density of 6.25× $10^4$ mm−2, equivalent to about 6 nanoneedles within a cell contacting area. The tops of the channels have herringbone grooves for generating internal spinning flow streams as the cells are flowing through the device, promoting cell-nanoneedle collisions for cytosolic delivery of DNA and biomacromolecules, such as siRNA, ASO, peptide and protein. A variety of cells are described for use, including difficult-to-transfect cells, e.g., stem cells, neuron cells and immune cells. Numerous target Hek293A cells (human embryonic kidney cells) were suspended in a fluid with GFP plasmids then flowed through the device under the grooves and over the nanoneedles. An approximate 20% transfection rate was associated with 95% viability. The highest rate of transfection, 25%, was associated with 85-90% viability. Although this reference device has channels lined with nanoneedles, unlike the disclosed device there is no description of poration of cells flowing in single file through a channel while being simultaneously squeezed and poked by nanospikes for intracellular delivery of a compound.

Yet another example of a device is described in Sharei, WO2016070136. "Delivery of biomolecules to immune cells." Applicant Massachusetts Institute of Technology. Filed Oct. 30, 2016. This reference describes a microfluidic electroporation system for generating holes in a cell's plasma membrane by squeezing cells. i.e. lymphocytes, for intracellular delivery of compounds. The device has channels for simultaneously constricting cells moving one cell at a time while moving through an electric field for prorating the cell. Treated cells may be used for drug screening, dosage studies and as a therapeutic.

Although this reference a microfluidic device for porating cells moving in single file through a channel while simultaneously being constricted for generating holes and exposed to an electric field allowing intracellular delivery of compounds, this reference does not describe poration of cells flowing in single file through a channel while being simultaneously squeezed and poked by nanospikes for intracellular delivery of a compound.

Sharei also has a paper publication, as Sharei, et al., Jensen, "A vector-free microfluidic platform for intracellular delivery." PNAS 110 (6):2082-2087 (2013). This reference describes a physical constriction to deform cells within channels of a microfluidic device for allowing for delivery of macromolecules suspended in the fluid with the cells. Although not explicitly described, figures show one cell at a time moving through the constricting channel, for generating transient membrane holes allowing for intracellular delivery. Cells containing Dextran were around 20-60%, with viability up to 70% for murine lymphocytes. Macromolecules included proteins, and siRNA, delivered to 11 different cell types, including mouse embryonic stem cells, human fibroblasts, HeLa cells, a human cancer cell line, human colon cancer cell line HT-29 and mouse immune cells, i.e. mouse lymphocytes. A family of microfluidic devices with different constriction dimensions and numbers of constrictions in series was also discussed. Although this reference a microfluidic device for porating cells moving in single file through a channel while being constricted for generating holes allowing intracellular delivery of compounds, this reference does not explicitly describe poration of cells flowing in single file through a channel while being simultaneously squeezed and poked by nanospikes for intracellular delivery of a compound.

Cell squeezing alone is described in "Our Science". CellSqueeze, SQZ Biotechnologies, sqzbiotech.com. Downloaded Mar. 14, 2019. This reference describes CellSqueeze's microfluidic system, announced in 2013 (see, The Scientist (Narrow Straits: Transfecting molecules into cells is as easy as one, two, squeeze. Williams, Jul. 1, 2013), that can deliver a variety of materials, including siRNA, drugs, proteins, or nanoparticles, into virtually any cell type. (See "Narrow Straits," The Scientist, July 2013.) The system uses a rectangular microfluidic chip containing a series of 75 parallel channels, each of which is 30 microns in diameter and contains at least one narrow constriction designed to be smaller than the diameter of a cell. As the cells squeeze through the constrictions, extracellular molecules to enter the cytoplasm by diffusion.

Users simply add their material to be transfected to a sample of cells in solution, deposit the mixture into the one of the interchangeable reservoirs, and apply pressure to begin pumping the sample through the device. Cells that have passed through the chip collect in the opposite reservoir, where they can be retrieved.

V. Microfluidic Devices.

As used herein, the term "microfluidics system" refers to systems in which low volumes (e.g., nL, pL, fL) of fluids are processed to achieve the discrete treatment of small volumes of liquids. Certain implementations described herein include multiplexing, automation, and high throughput screening. The fluids (e.g., a buffer, a solution, a payload-containing solution, or a cell suspension) can be moved, mixed, separated, or otherwise processed. In certain embodiments described herein, microfluidics systems are used to induce perturbations (e.g., holes) in the cell membrane that allow a payload or compound to enter the cytosol of the cell. In some embodiments, the microfluidics systems described herein comprise a microfluidics device.

As used herein, a "microfluidic device" refers to a device comprising one or more microfluidics channels wherein the device is capable inducing temporary disruptions in a cell membrane and resulting in the cellular uptake of a payload that is present in the surrounding solution.

The terms "microfluidic channel" and "microfluidics flow channel" are used interchangeably herein and refer to a channel comprised within a microfluidics device through which a cell suspended in a solution (e.g., a cell suspension) can pass through. In some embodiments, the microfluidics channels described herein comprise an inlet, an outlet, a channel wall comprising an internal surface, and a perturbation zone comprising one or more perturbation features. For example, a cell suspension can enter the microfluidic device via an inlet of a microfluidics flow channel, pass through the microfluidics channel and the perturbation zone, and exit the microfluidics device via an outlet of the microfluidics flow channel. Passage of a cell through a perturbation zone induces temporary disruptions in the plasma membrane of the cell. These temporary disruptions are referred to herein as "perturbations." Perturbations created by the methods described herein are breaches in a cell that allow material from outside the cell to move into the cell. Non-limiting examples of perturbations include a hole, a tear, a cavity, an aperture, a pore, a break, a gap, or a perforation. The perturbations (e.g., pores or holes) created by the methods described herein are not formed as a result of assembly of protein subunits to form a multimeric pore structure such as that created by complement or bacterial hemolysins. The microfluidics devices described herein may also be referred to as "intracellular delivery tools."

The terms "payload". "cargo", "delivery material", "foreign molecule" are used interchangeably herein and encompass any material to be intracellularly delivered to a cell. Payloads can included, but are not limited to, proteins, small molecules, nucleic acids (e.g. RNA and/or DNA), modified nucleic acids, lipids, carbohydrates, macromolecules, vitamins, natural and synthetic molecules and polymers thereof, fluorescent dyes and fluorophores, carbon nanotubes, quantum dots, nanoparticles, expression vectors, nucleoproteins, organic and inorganic molecules and polymers thereof, and steroids. In some embodiments, a payload comprises a nucleic acid and a protein. In some embodiments, a payloads comprises a gene editing system such as TALENs, CRISPR/Cas9, and zinc-finger nucleases.

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

We claim:

1. A method, comprising:
   a) providing;
      i) a fluid comprising a nucleic acid and a plurality of target cells;
      ii) a fluidic poration device comprising a plurality of channels, each of said plurality of channels having a surface;
      iii) at least one nanostructure positioned on said surface;
   b) introducing said fluid into said each of said plurality of channels;
   c) piercing said each of said plurality of target cells the same number of times and to the same depth with said nanostructure;
   d) transfecting said each of said plurality of target cells with an equivalent amount of said nucleic acid.

2. The method of claim 1, wherein said each of said plurality of channels has a height and width, wherein said height or said width, or said height and said width, is smaller than an average diameter of said plurality of target cells.

3. The method of claim 1, wherein said each of said plurality of channels restricts entry to one of said plurality of target cells at a time.

4. The method of claim 1, wherein said each of said plurality of target cells comprise a cell membrane.

5. The method of claim 1, wherein said each of said plurality of target cells comprise a nuclear membrane.

6. The method of claim 4, wherein said piercing porates said cell membrane.

7. The method of claim 5, wherein said piercing porates said nuclear membrane.

8. The method of claim 7, wherein said transfecting further comprises gene editing.

9. The method of claim 1, wherein said nucleic acid is selected from the group consisting of a plasmid, a messenger ribonucleic acid, a small interfering ribonucleic acid, a short hairpin ribonucleic acid, a ribonucleic acid, a deoxyribonucleic acid and an oligonucleotide.

10. The method of claim 1, wherein said at least nanostructure is positioned in-series, as a single file row, or down the length of said surface.

11. The method of claim 1, wherein said each of said plurality of channels is configured with a shape selected from the group consisting of a circle, an ellipse, an elongated slit, a rectangle, a square, a hexagon, and a triangle.

12. The method of claim 1, wherein said at least one nanostructure is solid.

13. The method of claim 1, wherein said at least one nanostructure is not hollow.

14. The method of claim 1, wherein two nanostructures simultaneously pierce said each of said plurality of target cells in series.

15. The method of claim 1, wherein said equivalent amount of said nucleic acid is delivered in 50%-100% of said plurality of target cells.

16. The method of claim 1, wherein said transfected target cells are 95%-100% viable.

17. The method of claim 6, wherein said nucleic acid is delivered into the cytoplasm of said each of said plurality of target cells.

18. The method of claim 7, wherein said nucleic acid is delivered into the nucleus of said each of said plurality of target cells.

19. The method of claim 1, wherein said piercing creates a pore having a standard size.

20. The method of claim 4, further comprising resealing said porated cell membrane.

21. The method of claim 5, further comprising resealng said porated nuclear membrane.

22. The method of claim 1, wherein said nanostructure is selected from the group consisting of a nanoneedle, a nanospike and a nanolancet.

* * * * *